US009056114B2

(12) United States Patent
Erickson

(10) Patent No.: US 9,056,114 B2
(45) Date of Patent: Jun. 16, 2015

(54) CHEMICAL INDUCTION OF LACTATION

(75) Inventor: Jeffrey P. Erickson, East Woodstock, CT (US)

(73) Assignee: Jeffrey P. Erickson, East Woodstock, CT (US)

( * ) Notice: Subject to any disclaimer, the term of this patent is extended or adjusted under 35 U.S.C. 154(b) by 0 days.

(21) Appl. No.: 13/392,650

(22) PCT Filed: Aug. 27, 2010

(86) PCT No.: PCT/US2010/002357
§ 371 (c)(1),
(2), (4) Date: Mar. 26, 2012

(87) PCT Pub. No.: WO2011/025540
PCT Pub. Date: Mar. 3, 2011

(65) Prior Publication Data
US 2012/0178686 A1    Jul. 12, 2012

Related U.S. Application Data

(60) Provisional application No. 61/237,867, filed on Aug. 28, 2009, provisional application No. 61/248,678, filed on Oct. 5, 2009.

(51) Int. Cl.
| A61K 31/56 | (2006.01) |
| A61K 38/12 | (2006.01) |
| A61K 38/11 | (2006.01) |
| A61K 38/10 | (2006.01) |
| A61K 38/04 | (2006.01) |
| A61P 15/14 | (2006.01) |

(52) U.S. Cl.
CPC ...................................... A61K 31/56 (2013.01)

(58) Field of Classification Search
CPC ... A61K 31/56; A61K 31/00; A61K 2300/00; A61K 38/11; A61K 38/10; A61K 38/04; A61K 38/00; C07K 7/64; C07K 7/00
USPC ........................................................ 514/11.6
See application file for complete search history.

(56) References Cited

U.S. PATENT DOCUMENTS

| 4,981,785 | A | 1/1991 | Nayak | 435/7 |
| 5,358,691 | A | 10/1994 | Clark | 422/64 |
| 5,372,818 | A | 12/1994 | Cross | 424/442 |
| 5,538,848 | A | 7/1996 | Livak | 435/6 |
| 5,582,592 | A | 12/1996 | Kendrick | 604/55 |
| 5,599,677 | A | 2/1997 | Dowell | 435/7.4 |
| 5,639,606 | A | 6/1997 | Willey | 435/6 |
| 5,643,765 | A | 7/1997 | Willey | 435/91.2 |
| 5,672,480 | A | 9/1997 | Dowell | 435/7.4 |
| 5,705,188 | A | 1/1998 | Yano | 424/450 |
| 5,846,717 | A | 12/1998 | Brow | 435/6 |
| 5,876,978 | A | 3/1999 | Willey | 435/91.2 |
| 5,885,530 | A | 3/1999 | Babson | 422/65 |
| 5,985,557 | A | 11/1999 | Prudent | 435/6 |
| 5,994,069 | A | 11/1999 | Hall et al. | 435/6 |
| 6,001,567 | A | 12/1999 | Brow | 435/6 |
| 6,090,543 | A | 7/2000 | Prudent | 435/6 |
| 6,159,750 | A | 12/2000 | Edmonds | 436/537 |
| 6,844,322 | B2 * | 1/2005 | McGrath et al. | 514/11.3 |
| 2001/0005724 | A1 * | 6/2001 | Cross | 514/322 |
| 2005/0246781 | A1 | 11/2005 | Erickson | 800/8 |
| 2006/0287228 | A1 | 12/2006 | Velander et al. | 512/12 |

FOREIGN PATENT DOCUMENTS

| WO | WO/97/30731 | 8/1997 | |
| WO | WO 2007/139826 | * 12/2007 | A61K 38/07 |

OTHER PUBLICATIONS

Erb, Journal of Dairy Science (1976) vol. 60, No. 7, pp. 155-169.*
Powell et al., Journal of Dairy Research (2007), 74, 247-254.*
Ball et al., J Dairy Sci (2000) 83, 2459-2463.*
Ballou et al., J Dairy Science (1993) 76, 1544-1549.*
Armstrong, W. E. et al. (2006) "The puzzle of pulsatile oxytocin secretion during lactation: some new pieces," *American Journal of Physiology—Regulatory, Integrative and Comparative Physiology* 291(1), R26-R28.
Baldassarre, H. et al. (2008) "Lactation performance of transgenic goats expressing recombinant human butyryl-cholinesterase in the milk," *Transgenic Research* 17(1), 73-84.
Ball, S. et al. (2000) "Induced Lactation in Prepubertal Holstein Heifers," *Journal of Dairy Science* 83(11), 2459-2463.
Britt, J. H. et al., (1985) "Control of follicular development during and after lactation in sows," *J. Reprod. Fertil. Suppl.* 33, 37-54.
Chavatte-Palmer, P. et al. (2002) "Quantitative and Qualitative Assessment of Milk Production after Pharmaceutical Induction of Lactation in the Mare," *Journal of Veterinary Internal Medicine* 16(4), 472-477.
Clark, A. J., (1989) "Expression of human anti-hemophilic factor IX in the milk of transgenic sheep," *Bio/Technology* 7, 487-492.
Clowes, E. J. et al. (1998) "Feeding lactating primiparous sows to establish three divergent metabolic states: II. Effect on nitrogen partitioning and skeletal muscle composition," *Journal of Animal Science* 76(4), 1154-1164.
Denman, J. et al. (1991) "Transgenic expression of a variant of human tissue-type plasminogen activator in goat milk: purification and characterization of the recombinant enzyme," *Bio/Technology* 9(9), 839-843.

(Continued)

*Primary Examiner* — Karlheinz R Skowronek
*Assistant Examiner* — Catherine Mader
(74) *Attorney, Agent, or Firm* — Medlen & Carroll, LLP

(57) ABSTRACT

The present invention describes a method of inducing lactation in non-human mammals by using a single administrations of an estrogen compound, a dopaminergic antagonist, and oxytocin. For example, the estrogen compound may be a long acting composition and is administered at least one week before the dopaminergic antagonist. However, the oxytocin administration may be given the day after the dopaminergic antagonist, after which lactation may begin immediately. Preferred compounds may comprise a non-17β estradiol and domperidone. Such an injection protocol has resulted in the production of commercially viable volumes of milk from transgenic pigs.

19 Claims, 2 Drawing Sheets

(56) References Cited

OTHER PUBLICATIONS

Drohan, W. et al. (1994) "Inefficient processing of human protein C in the mouse mammary gland," *Transgenic Research 3*(6), 355-364.

Gabay, M. P. (2002) "Galactogogues: Medications That Induce Lactation," *Journal of Human Lactation 18*(3), 274-279.

Henderson, A. (2003) "Domperidone," *AWHONN Lifelines 7*(1), 54-60.

Lee, T. K. et al. (1995) "Proteolytic Processing of Human Protein C in Swine Mammary Gland," *The Journal of Biochemistry 118*(1), 81-87.

Lezica, F. P. et al. (2009) "Prevalence of ergot derivatives in natural ryegrass pastures: Detection and pathogenicity in the horse," *Theriogenology 71*(3), 422-431.

Luboń, H. et al. (1996) "Blood proteins from transgenic animal bioreactors," *Transfusion Medicine Reviews 10*(2), 131-143.

Marasco, L. (2008) "ILCA's Inside Track A of the International Lactation Consultant Association: Increasing Your Milk Supply With Galactogogues," *Journal of Human Lactation 24*(4), 455-456.

Morcol, T. et al. (1994) "The Porcine Mammary Gland as a Bioreactor for Complex Proteinsa," *Annals of the New York Academy of Sciences 721*(1), 218-233.

Paleyanda, R. K. et al. (1997) "Transgenic pigs produce functional human factor VIII in milk," *Nature Biotechnology 15*(10), 971-975.

Sambrook, J. et al. (1989) "Synthesis of Single-stranded RNA Proves by In Vitro Transcription," in *Molecular Cloning: A Laboratory Manual* (Sambrook, J., et al., Eds.) 2nd ed., pp. 9.31-9.58, Cold Spring Harbor Laboratory Press, New York.

Sambrook, J. et al. (1989) "Transfer and Fixation of Denatured RNA to Membranes," in *Molecular Cloning: A Laboratory Manual* (Sambrook, J., et al., Eds.) 2nd ed., pp. 7.39-7.52, Cold Spring Harbor Laboratory Press, New York.

Shamay, A. et al., (1992) "Induction of lactogenesis in transgenic virgin pigs: evidence for gene and integration site-specific hormonal regulation," *Mol. Endocrinol. 6*(2), 191-197.

Van Cott, K. E. et al. (2004) "Haemophilic factors produced by transgenic livestock: abundance that can enable alternative therapies worldwide," *Haemophilia 10*, 70-76.

Velander, W. H. et al. (1992) "High-level expression of a heterologous protein in the milk of transgenic swine using the cDNA encoding human protein C," *Proceedings of the National Academy of Sciences 89*(24), 12003-12007.

Wan, E. W. X. et al. (2008) "Dose-effect study of domperidone as a galactagogue in preterm mothers with insufficient milk supply, and its transfer into milk," *British Journal of Clinical Pharmacology 66*(2), 283-289.

Wheeler, M. B. (2003) "Production of transgenic livestock: Promise fulfilled," *Journal of Animal Science 81*(suppl 3), 32-37.

Yarus, S. et al. (1997) "Secretion of unprocessed human surfactant protein B in milk of transgenic mice," *Transgenic Research 6*(1), 51-57.

\* cited by examiner

| Day | Oxytocin | Raw Milk | ACA | RM + ACA | EDTA |
|-----|----------|----------|-----|----------|------|
| 1   | 4        | 27       | 5   | 32       | 32   |
| 2   | 5        | 97.5     | 4   | 101.5    | 101.5|
| 3   | 4        | 160      | 5   | 165      | 165  |
| 4   | 4        | 305      | 5   | 310      | 310  |
| 5   | 4        | 248      | 10  | 258      | 258  |
| 6   | 4        | 210      | 10  | 220      | 220  |
| 7   | 4        | 220      | 10  | 230      | 230  |
| 8   | 4        | 260      | 10  | 270      | 270  |
| 9   | 4        | 100      | 10  | 110      | 110  |
| 10  | 4        | 76       | 5   | 81       | 81   |
| 11  | 0        | 0        | 0   | 0        | 0    |
| 12  | 3        | 237      | 10  | 247      | 247  |
| 13  | 3        | 40       | 5   | 45       | 45   |
| 14  | 3        | 90       | 5   | 95       | 95   |
| 15  | 4        | 69       | 5   | 74       | 74   |
| 16  | 4        | 152      | 10  | 162      | 162  |
| 17  | 4        | 43       | 5   | 48       | 48   |
| 18  | 4        | 50       | 10  | 60       | 60   |
| 19  | 4        | 10       | 5   | 15       | 15   |
| 20  | 4        | 82.5     | 5   | 87.5     | 87.5 |
| 21  | 4        | 9        | 5   | 14       | 14   |

Figure 1

| Day | Oxytocin #1 | Oxytocin #2 | Raw Milk | ACA | RM + ACA | EDTA |
|---|---|---|---|---|---|---|
| 1 | 5 | 5 | 2 | 2 | 4 | 4 |
| 2 | 7 | 0 | 3 | 5 | 8 | 8 |
| 3 | 7 | 0 | 7.5 | 5 | 12.5 | 12.5 |
| 4 | 10 | 5 | 8 | 5 | 13 | 13 |
| 5 | 10 | 0 | 18 | 5 | 23 | 23 |
| 6 | 8 | 5 | 3.5 | 5 | 8.5 | 8.5 |
| 6 | 10 | 0 | 5.5 | 5 | 10.5 | 10.5 |
| 7 | 10 | 3 | 5 | 5 | 10 | 10 |
| 7 | 8 | 3 | 3.5 | 5 | 8.5 | 8.5 |
| 8 | 10 | 0 | 1 | 5 | 6 | 6 |
| 8 | 8 | 0 | 2 | 5 | 7 | 7 |
| 9 | 7 | 0 | 0.5 | 5 | 5.5 | 5.5 |
| 9 | 7 | 0 | 1 | 5 | 6 | 6 |
| 10 | 7 | 0 | 0.5 | 5 | 5.5 | 5.5 |
| 11 | 0 | 0 | 0 | 0 | 0 | 0 |
| 12 | 0 | 0 | 0 | 0 | 0 | 0 |
| 13 | 0 | 0 | 0 | 0 | 0 | 0 |
| 14 | 4 | 0 | 118 | 5 | 123 | 123 |
| 15 | 4 | 0 | 230 | 10 | 240 | 240 |
| 16 | 5 | 0 | 385 | 15 | 400 | 400 |
| 17 | 5 | 0 | 295 | 15 | 310 | 310 |
| 18 | 6 | 0 | 240 | 10 | 250 | 250 |
| 19 | 4 | 0 | 315 | 15 | 330 | 330 |
| 20 | 6 | 0 | 107 | 5 | 112 | 112 |
| 21 | 4 | 0 | 40 | 5 | 45 | 45 |
| 22 | 4 | 0 | 60 | 5 | 65 | 65 |
| 23 | 4 | 0 | 21 | 5 | 26 | 26 |

CHEMICAL INDUCTION OF LACTATION

FIELD OF INVENTION

The present invention is related to the field of transgenic animals. Specifically, the invention is related to the expression of transgenic proteins in the milk of mammals. Lactation inducers have been utilized to optimize the production and collection of milk from transgenic mammals. It is contemplated that lactation may be induced in either male or female swine using a combination of a non-17β estradiol, domperidone and oxytocin.

BACKGROUND

The therapeutic protein market is estimated to surpass $90 billion by 2010. Anonymous. "Therapeutic Proteins: Research Report" *Lead Discovery Ltd.* (2005). Therapeutic proteins such as hormones, enzymes, peptides and antibiotics for use in disease therapy have been extracted from human plasma, animal tissues, or produced by recombinant DNA technology. These proteins are used to treat various cancers, heart attacks, stroke, cystic fibrosis, Gaucher's disease, diabetes, anemia and hemophilia. It is important that such products are free of blood-borne pathogens derived from human and animal tissues, thereby making manufacturing costs and capacity concerns that affect the successful commercialization of the therapeutic protein market.

Presently, an inadequate protein supply and viral safety concerns surrounding plasmid-derived proteins have led to the development of recombinant production of therapeutic proteins. While genetically engineered plants, bacteria and yeast are adequate for producing simple mammalian proteins, they lack the cellular machinery to perform the complex protein glycosylation, carboxylation, assembly of subunits and folding (post-translational modification (PTM)), for biological activity.

Consequently, it is a long felt need in the art to develop technology such that large amounts of transgenic proteins may be economically collected and processed from non-human transgenic mammals.

SUMMARY

The present invention is related to the field of transgenic animals. Specifically, the invention is related to the expression of transgenic proteins in the milk of mammals. Lactation inducers have been utilized to optimize the production and collection of milk from transgenic mammals. It is contemplated that lactation may be induced in either male or female swine using a combination of a non-17β estradiol, domperidone and oxytocin.

In one embodiment, the present invention contemplates a method, comprising: a) providing; i) a first composition comprising an estrogen compound, wherein said first composition is a pharmaceutically acceptable formulation; ii) a second composition comprising a dopaminergic antagonist, wherein said second composition is a pharmaceutically acceptable formulation; iii) a third composition comprising oxytocin, wherein said third composition is a pharmaceutically acceptable formulation; iii) a non-pregnant mammal; b) administering a single dose of said first composition to said mammal; c) administering a single dose of said second composition to said mammal; and d) administering a single dose said third composition to said mammal. In one embodiment, the estrogen compound is long acting. In one embodiment, the third composition is administered on a daily basis after administering the second composition.

In one embodiment, the present invention contemplates a method for inducing lactation in non-pregnant animals by administering a combination of estradiol, domperidone, and oxytocin. In one embodiment, the estradiol is not a 17β-estradiol. In one embodiment, the combination of estradiol, domperidone, and oxytocin is administered to the mammal sequentially. In one embodiment, the combination of estradiol, domperidone, and oxytocin is administered to the mammal simultaneously. In one embodiment, the sequential administration comprises a separation of at least one hour. In one embodiment, the sequential administration comprises a separation of at least six hours. In one embodiment, the sequential administration comprises a separation of at least twelve hours. In one embodiment, the sequential administration comprises a separation of at least one day. In one embodiment, the sequential administration comprises a separation of at least three days. In one embodiment, the sequential administration comprises a separation of at least seven days. In one embodiment, the sequential administration comprises a separation of at least fourteen days. In one embodiment, the method further comprises an administration of a pharmaceutically acceptable formulation comprising altrenogest. In one embodiment, the estradiol is long acting.

In one embodiment, the present invention contemplates a method, comprising: a) providing; i) a first composition comprising a non-17β estradiol, wherein said first composition is a pharmaceutically acceptable formulation; ii) a second composition comprising domperidone, wherein said second composition is a pharmaceutically acceptable formulation; iii) a third composition comprising oxytocin, wherein said third composition is a pharmaceutically acceptable formulation; iii) a non-pregnant mammal; b) administering a single dose of said first composition to said mammal; c) administering a single dose of said second composition to said mammal; d) administering a single dose said third composition to said mammal. In one embodiment, the method further comprises step (e) collecting a commercially viable volume of milk from said mammal. In one embodiment, the second composition is administered fourteen days after said first composition. In one embodiment, the third composition is administered twenty-four hours after said second composition. In one embodiment, the third composition is administered on a daily basis after said second composition. In one embodiment, the first composition is administered orally. In one embodiment, the second composition is administered orally. In one embodiment, the third composition is administered parenterally. In one embodiment, the parenteral administration comprises an intramuscular injection. In one embodiment, the oral administration comprises a gel. In one embodiment, the milk is collected on the same day as said oxytocin administration. In one embodiment, the non-pregnant mammal is a female. In one embodiment, the non-pregnant mammal is a male. In one embodiment, the female mammal is nulliparous. In one embodiment, the female mammal has not been pregnant for at least six months. In one embodiment, the female mammal has not been pregnant for at least twelve months. In one embodiment, the female mammal has delivered at least one litter. In one embodiment, the female mammal is a virgin. In one embodiment, the female mammal is prepubertal. In one embodiment, the non-17β estradiol is long acting.

DEFINITIONS

The term "dopaminergic antagonist" as used herein, refers to any compound that reduces the functionality of the neurotransmitter, dopamine. For example, a dopaminergic antagonist may include, but is not limited to, a dopamine receptor antagonist, a dopamine synthesis inhibitor, or a dopamine reuptake enhancer. Examples of a dopamine receptor antagonist include, but are not limited to, domperidone, metoclopramide, or sulpiride.

The term "estrogen compound" as used herein, refers to any compound based upon an estrogen steroid ring structure. For example, an estrogen compound may include, but is not limited to, 17β-estradiol, 17α-estradiol, a non-17β estradiol, estradiol derivatives, and estradiol salts.

The term 'lactation" as used herein, refers to any secretion and/or yielding of milk by the mammary gland. Normally, a complete lactation period extends from about the time of parturition to weaning.

The term "nulliparous" as used herein, refers to any animal (i.e., for example, a mammal) that has not borne offspring.

The term "not been pregnant" as used herein, refers to any animal (i.e., for example, a mammal) that has not carried a developing embryo. Normally, pregnancy is a result of in vivo breeding but also may result from in vitro fertilization and implantation technology.

The term "barren" as used herein, refers to any animal (i.e., for example, a mammal) that is incapable of bearing offspring.

The term "commercially viable volume" as used herein, refers to a minimal daily lactated milk volume per animal that results in efficient and profitable processing and distribution of secreted proteins (i.e., for example, a transgenic protein). For example, a commercially viable volume may range between approximately 0.06-60 L/day/animal. More preferably, between 3-40 L/day/animal. Most preferably between 5-20 L/day/animal. 140/9*3.6=

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "inhibitory compound" as used herein, refers to any compound capable of interacting with (i.e., for example, attaching, binding etc) to a binding partner under conditions such that the binding partner becomes unresponsive to its natural ligands. Inhibitory compounds may include, but are not limited to, small organic molecules, antibodies, and proteins/peptides. The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository etc.

The term "derived from" as used herein, refers to the source of a compound or sequence. In one respect, a compound or sequence may be derived from an organism or particular species. In another respect, a compound or sequence may be derived from a larger complex or sequence. The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation, electrophoresis) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide. "Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

BRIEF DESCRIPTION OF THE FIGURES

FIG. 1 presents exemplary data from a non-pregnant sow (ID: Granny) showing volumes of a daily collection of chemically induced milk. Oxytocin: Volume of daily pre-collection injection. ACA: 6-aminocaproic acid. RM: Raw milk. EDTA: Ethylenediamine tetraacetic acid. All data expressed in milliliters.

FIG. 2 presents exemplary data from a gilt (ID: Sis) showing volumes of a daily collection of chemically induced milk. Oxytocin: Volume of daily pre-collection injection. ACA: 6-aminocaproic acid. RM: Raw milk. EDTA: Ethylenediamine tetraacetic acid. All data expressed in milliliters.

DETAILED DESCRIPTION OF THE INVENTION

The present invention is related to the field of transgenic animals. Specifically, the invention is related to the expression of transgenic proteins in the milk of mammals. Lactation inducers have been utilized to optimize the production and collection of milk from transgenic mammals. It is contemplated that lactation may be induced in either male or female swine using a combination of a non-17β estradiol, domperidone and oxytocin.

The present invention contemplates methods of producing commercially viable volumes of milk in transgenic animals. In some embodiments, the present invention contemplates inducing lactation in a transgenic swine. Despite the previous research reported for various compounds, combinations, and protocols, none have been reported to produce commercially viable volumes of milk in swine. As detailed below, current methods reported to induce lactation using chemicals including 17β-estradiol, domperidone, and/or oxytocin has not produced commercially viable volumes of milk in any mammal. Furthermore, these reported methods all utilize repeated injections of the compounds, and have not found the unexpected and surprising combination of single doses administered on different days.

I. Repeated Administration of Galactogogues

It has been reported that most galactogogues (i.e., compounds facilitating milk production) interact with dopamine receptors, thereby increasing prolactin levels. A galactogogue is usually defined as a compound useful in females who are unable to produce breast milk on their own due to: i) infant prematurity; ii) illness of the mother or child, iii) adoption; or iv) surrogate motherhood. Domperidone and oxytocin be of assistance mothers of premature newborns that were unable to complete the normal hormonal parturition cycle. Gabay M. P., "Galactogogues: medications that induce lactation" *J Hum Lact*. 18:274-279 (2002).

The induction of lactation in non-pregnant horses (i.e., for example, mares) has been reported by: i) administering a vaginal pessary having a combination of altrenogest and estradiol for one week; and ii) during the second week a replacement estradiol pessary (at double the dose of the first pessary) was administered in combination with a twice daily administration of either: a) oxytocin, b) sulpiride; or c) domperidone. Most mares treated with sulpiride or domperidone demonstrated an induction of lactation (~1 liter per mare/day) within 2-5 days after commencing administration. Nonetheless, these volumes are below that what is observed in a normal lactating postpartum mare and were not sufficient to feed a suckling foal. Further, while milk IgG contents increased in all mares before the onset of lactation, overall the quantities of high-quality secretions were low (i.e., for example, 250 mL). Specifically, milk protein concentrations decreased significantly during the seven days of sulpiride treatment leading up to the establishment of lactation. Specifically, this reference demonstrates that lactation can be induced in non-pregnant mares within 7-12 days after the beginning of treatment by means of a progesterone and estrogen treatment, followed by sulpiride or domperidone. Chavatte-Palmer et al., "Quantitative and qualitative assessment of milk production after pharmaceutical induction of lactation in the mare" *J Vet Intern Med*. July-August; 16:472-477 (2002).

The administration of domperidone to promote lactation has been reported in pregnant female mammals expected to be agalactic. Domperidone administered to the mammal either orally or subcutaneously is suggested to begin approximately fifteen—twenty days before parturition. Cross et al., "Method for promoting ovulation, parturition, and lactation in mammals" U.S. Pat. No. 6,455,546 (herein incorporated by reference). Agalactia is usually defined as a condition wherein a postpartum female fails to undergo mammary development and is therefore incapable of lactation.

The administration of domperidone for at least eighteen (18) days has been reported to increase lactation in gravid horses suffering from endophyte-infected ryegrass toxicity, a condition that reduces milk production. Lezica et al., "Prevalence of ergot derivatives in natural ryegrass pastures: detection and pathogenicity in the horse" *Theriogenology* 1:422-431 (2009). A second report discusses observations that the administration of domperidone or sulpiride to gravid equine mares suffering from endophyte-infected ryegrass toxicity for thirty days before foaling increases udder development. Cross et al., "Method of treating fescue toxicosis with domperidone" U.S. Pat. No. 5,372,818 (herein incorporated by reference).

Domperidone may follow a dose-response relationship for treating insufficient milk supply in mothers of preterm infants. The reference does not suggest that domperidone will induce lactation in a non-pregnant mammals, either alone, or in combination with oxytocin. Wan et al., "Dose-effect study of domperidone as a galactagogue in preterm mothers with insufficient milk supply, and its transfer into milk" *Br J Clin Pharmacol.* 66 (2):283-289 (2008)

The hormonal induction of lactation was demonstrated in six prepuberal Holstein heifers. Specifically, a twenty (20) day series of injection of estrogen (i.e., 17β-estradiol) and progesterone (seven injections) was followed by dexamethasone (three injections). This injection regimen was capable of inducing milk secretion in the range of 31-800 ml/day. The reference does not suggest induction of lactation by either domperidone or oxytocin, ether alone or in combination. Ball et al., "Induced Lactation in Prepubertal Holstein Heifers" *J Daily Sci* 83:2459-2463 (2000).

II. Induction of Lactation in Swine

In one embodiment, the present invention contemplates that an efficient production of large amounts of complex recombinant protein can be obtained by using the mammary gland of livestock (i.e., for example, goats, cows, pigs etc.) as a production "bioreactor". Pursel et al., "Recent Progress in the Transgenic Modification of swine and sheep" *Mol Reprod and Dev.* 36:251-254 (1993); Morcol et al., "The porcine mammary gland as a bioreactor for complex proteins" *Annals of the New York Academy of Sciences* 721:218-233 (1994); and Lubon et al., "Blood proteins from transgenic animal bioreactors" *Transfus Med. Rev.* 0:131-143 (1996). The swine mammary gland is reported capable of having the post-translational processing machinery to efficiently process most transgenic proteins thereby resulting in biological activity and long circulation half-life needed for therapeutic applications. Van Cott et al., "Haemophilic factors produced by transgenic livestock: Abundance that can enable alternative therapies worldwide" *Haemophilia* 10 (4):70-76 (2004). For example, it has been reported that transgenic pig milk can be a prodigious and expedient source of complex therapeutic proteins relative to cell culture bioreactors. Lubon et al., "Blood proteins from transgenic animal bioreactors" *Transfus Med Rev.* 10:131-143 (1996). When considered as potential bioreactors, mammary tissues can produce high concentrations of secreted proteins, owing to the high cell density of the gland, with about $10^9$ cells/mL of tissue. This cell density is believed to be 2 to 3 orders of magnitude greater than that possible in mammalian cell-culture production technology used to make complete recombinant therapeutic proteins, thereby resulting in high protein production rates of about 1-15 g/L/h. Van Cott et al., "Haemophilic factors produced by transgenic livestock: Abundance that can enable alternative therapies worldwide" *Haemophilia* 10 (4):70-76 (2004). Other advantages that pigs offer over other dairy livestock includes, but are not limited to: i) a short gestation interval of 114 days; ii) production of 2.4 litters per year; and lactating approximately 10 kg milk per day. Wheeler, M B., "Production of transgenic livestock: Promise fulfilled" *J Anim Sci.* 81:32-37 (2003); and Table 1.

TABLE 1

Reproductive and lactation characteristics of animal species commonly used for expression of recombinant proteins in milk

| Species | Reproductive age (mo.) | Length of gestation (mo.). | Avg. number of offspring | Avg. % of transgenic birth | Avg. milk yield per lactation (l) |
|---|---|---|---|---|---|
| Mouse | 1 | 0.75 | 10 | 10-25 | 0.0015 |
| Rabbit | 6 | 1 | 8 | 5-15 | 1.5 |
| Pig | 8 | 4 | 9 | 5-15 | 120 |
| Sheep | 8 | 5 | 2 | 3-5 | 300-400 |
| Goat | 8 | 5 | 2 | 3-5 | 600-800 |
| Cattle | 15 | 9 | 1 | 0.5-3 | 10,000 |

As such, the short production interval in transgenic swine coupled with mammary cell mechanisms makes milk collection a more efficient bioreactor for production of recombinant proteins to be used in production and development of therapeutic compositions as compared to currently developed laboratory technologies. For example, Chinese Hamster Ovary and Human Kidney 293 in vitro cell lines can make and secrete active transgenic proteins at about 10 pg/cell/day in the context of a large scale bioreactor setting. This is equivalent to about 10-30 μg/ml/72 hours of recombinant protein accumulated in an in vitro bioreactor. While some in vitro bioreactors under development eventually expect cell densities from 5-50 million cells per milliliter of culture broth, the mammary gland of livestock comprises about 1 billion epithelial cells per milliliter of secreted milk.

In one embodiment, the present invention contemplates a method comprising producing about 300 to 1000 μg/ml/hour (i.e., for example, approximately 0.3 to 1 g/l/hour) of biologically active transgenic protein in swine milk. Although it is not necessary to understand the mechanism of an invention, it is believed that pigs let their milk down every hour thereby producing a concentration between approximately 0.01 to 10 g/l of these proteins. In one embodiment, the method further comprises collecting at least three milk letdowns per day. In one embodiment, the method further comprising inducing lactation in an individual transgenic pig at least twice a year, wherein the lactation is induced for a plurality of days. In one embodiment, the plurality of days comprises fifty days. In one embodiment, the method further comprises producing at least 100 liters of milk per year in each individual transgenic pig. In one embodiment, the method further comprises producing between approximately 30 to 300 grams of recombinant transgenic protein per year.

A. Dopaminergic Receptor Antagonists

In one embodiment, the present invention contemplates a method to induce lactation in a non-human mammal using a dopamine receptor antagonist. In one embodiment, the antagonist comprises domperidone. In one embodiment, the antagonist comprises metoclopromide. In one embodiment, the antagonist comprises sulpiride. In one embodiment, the antagonist comprises itopride. In one embodiment, the antagonist comprises benzamide. In one embodiment, the antagonist comprises cisapride. Although it is not necessary to understand the mechanism of an invention, it is believed that these dopaminergic receptor antagonists block primarily the $D_2$ and $D_3$ type dopamine receptors.

Domperidone is a representative dopamine-receptor blocking agent (i.e., for example, a dopaminergic receptor antagonist). Domperidone does not cross the blood-brain barrier to any appreciable degree and so exerts relatively little effect on cerebral dopaminergic receptors. Domperidone has been shown to increase the duration of antral and duodenal contractions to increase gastric emptying. Domperidone does not alter gastric secretions and has no effect on intracranial pressure or on the cardiovascular system. Domperidone is rapidly absorbed, with peak plasma concentrations at approximately 1 hour after oral administration. The absolute bio-availability of oral domperidone is low (approximately 15%) due to first-pass hepatic and intestinal metabolism. Domperidone is 91-93% bound to plasma proteins. The plasma half-life after a single oral dose is 7-9 hours in healthy subjects but is prolonged in patients with severe renal insufficiency. Domperidone undergoes rapid and extensive hepatic metabolism by hydroxylation and N-dealkylation. Urinary and fecal excretion amount to 31% and 66% of the oral dose, respectively. The proportion of drug excreted unchanged is small (approximately 1% of urinary and 10% of fecal excretion).

Domperidone is usually prescribed for conditions including, but not limited to: i) delayed gastric emptying of functional origin with gastro-oesophageal reflux and/or dyspepsia; ii) control of nausea and vomiting of central or local origin; iii) an anti-emetic in patients receiving cytostatic and radiation therapy; or iv) radiological examination of the upper gastro-intestinal tract. Dosing in adult humans using comprises the administration of two tablets (20 mg) 3 to 4 times per day to a human adult, 15 to 30 minutes before meals and, if necessary, before retiring.

Domperidone was observed to have a side effect that stimulated breast milk production in humans. Although it is not necessary to understand the mechanism of an invention, it is believed that this effect is achieved by an increase in pituitary prolactin production. Such an action may be a result of preventing dopaminergic inhibition of prolactin secretion.

In humans, lactating mothers may face a variety of challenges including maintaining a sufficient milk supply. Although there are a number of behavioral and other approaches to helping lactating mothers increase their milk. Domperidone has been discussed as a pharmaceutical intervention for lactating mothers to increase milk production, however, the domperidone is not approved for human use in the United States. Henderson, A., "Domperidone Discovering New Choices for Lactating Mothers" *AWHONN Lifelines* 7:54-60 (2003); and Marasco L., "Inside track. Increasing your milk supply with galactogogues" *J Hum Lact.* 24 (4): 455-456 (2008).

Metoclopramide (Maxeran®) is also a dopaminergic inhibitor that is believed to increase milk production, but has frequent side effects (i.e., for example, fatigue, irritability, depression). Domperidone's side effects include allergic reactions, stimulating or increasing milk production, by increasing prolactin production by the pituitary gland, such as rash or urticaria.

B. Estrogen Compounds

In one embodiment, the present invention contemplates a method to induce lactation in a non-human mammal using an estrogen compound. In one embodiment, the estrogen compound is a slow release compound. In one embodiment, the estrogen compound comprises a non-17β estradiol. In one embodiment, the estrogen compound comprises a 17β estradiol. In one embodiment, the estrogen compound comprises a 17α estradiol. In one embodiment, the estrogen compound comprises an estradiol derivative. In one embodiment, the estradiol derivative comprises ethinyl estradiol. In one embodiment, the ethinyl estradiol comprises 17α ethinyl estradiol. In one embodiment, the estrogen compound comprises an estradiol glucuronide. In one embodiment, the estradiol derivative comprises RU49953. In one embodiment, the estrogen compound comprises estradiol acetate. In one embodiment, the estrogen compound comprises estradiol cypionate. In one embodiment, the estrogen compound comprises estradiol hemihydrate. In one embodiment, the estrogen compound comprises estradiol valerate. In one embodiment, the estrogen compound comprises a phytoestrogen including, but not limited to, coumestrol, coumarol or zearalenone.

Estrogens have been reported to be involved in follicular development during early lactation in the sow, as characterized by a large population of small-sized follicles and a small population of medium-sized follicles. As lactation progresses there is a gradual shift in number of follicles into medium- or large-sized categories and the percentage of follicles classified as atretic declines. Weaning at birth often leads to aberrant follicular development, apparently because the positive feedback response of lutenizing hormone to estradiol does not occur during the first week post partum. Secretion of lutenizing hormone during lactation is primarily controlled by suckling intensity of the litter while follicular stimulating hormone is controlled by a nonsteroidal ovarian factor, presumably inhibin. Suckling apparently limits secretion of gonadotropin releasing hormone and weaning leads to an increase of gonadotropin releasing hormone within the hypothalamus coincident with an increase of lutenizing hormone in the anterior pituitary and plasma and increased follicular growth. Follicular development during both lactation and post-weaning anestrus can be stimulated by exogenous gonadotrophins and pulsatile administration of gonadotrophin releasing hormone. Factors such as nutrition, season, boar exposure, litter size and split weaning affect follicular development during lactation and after weaning, probably because they affect secretion of luteinizing hormone. Britt et al., "Control of follicular development during and after lactation in sows" *J Reprod Fertil Suppl.* 33:37-54 (1985).

Milk protein expression in prepuberal (five (5) month old) pigs implanted with time-release formulations of estrogen and progesterone has been observed. Histological analysis suggested hormonal induction of mammary alveoli within four (4) weeks after implantation. Nonetheless, milk collection or analysis was not assessed. Shamay et al., "Induction of Lactogenesis in Transgenic Virgin Pigs: Evidence for Gene and Integration Site-Specific Hormonal Regulation" *Mol Endocrinol* 6:191-197 (1992)

C. Oxytocin

Oxytocin is a nonapeptide hormone believed to play a role in lactation and parturition. Oxytocin's first described properties comprised uterine-contractions and sequenced. More recently, immunohistochemical studies revealed that magnocellular neurons of the hypothalamic paraventricular and supraoptic nuclei are the neurons of origin for oxytocin release from the posterior pituitary. Aside from oxytocin's role in reproduction, the hormone is also implicated in a variety of "non-social" behaviors, such as learning, anxiety, feeding and pain perception, social memory and attachment, sexual and maternal behavior, and aggression. Human disorders characterized by aberrant social interactions, such as autism and schizophrenia, may also involve oxytocin expression. Many, if not most, of oxytocin functions, from social interactions (affiliation, aggression) and sexual behavior to eventual parturition, lactation and maternal behavior, may be viewed as specifically facilitating species propagation.

Periodic bolus secretions of oxytocin from the neurohypophysis during suckling is believed responsible for providing sufficient milk to a nursing infant. Although it is not necessary to understand the mechanism of an invention, it is believed that pulsatile oxytocin release may maximize myoepithelial cell contractions in the mammary gland by avoiding receptor desensitization. Such periodicity comprises brief (i.e., for example, 4-6 seconds), synchronous, and explosive bursting of oxytocin-containing neurons. The bursting episodes occur over longer intervals (i.e., for example, 5-20 min). Oxytocin is believed to play multiple roles including, but not limited to, pregnancy, lactation, growth factor, and neuromodulators. Armstrong et al., "The puzzle of pulsatile oxytocin secretion during lactation: some new pieces" *Am J Physiol Regul Integr Comp Physiol* 291:R26-R28, 2006.

III. Collection of Mammary Transgenic Proteins

In one embodiment, the present invention contemplates using the lactation induction protocols described herein to effectively collect, purify, and determine biologic activity of recombinant human proteins (i.e., for example, prothrombin or clotting protein Factor II) from the milk of transgenic swine. Some recombinant proteins are commercially available, but not in an economy and supply that makes the development of therapies using these proteins commercially viable. For example, development of effective technologies may produce an economical, reliable and abundant source for prothrombin that is useful in making hemostatic dressings and fibrin sealants; with a secondary goal for purified prothrombin for human therapeutic applications (i.e. hypoprothrombinemia) for which there are currently no purified prothrombin products available Many enzymes and/or proteins are costly and difficult to make with currently used industrial bioreactor technology, especially when post-translational protein modifications are necessary (i.e., for example, γ-carboxylation). Previous research has indicated that the mammary epithelia of transgenic pigs have the capacity to efficiently produce transgenic proteins having post-translational modifications (data not shown). Relative to cell culture bioreactors, the milk of transgenic pigs can be a prodigious and expedient source of complex therapeutic proteins. For example, preliminary studies have demonstrated that each pig can potentially produce over 30 to 300 grams of recombinant protein per year. For some markets, between about 20 to 200 transgenic pigs would be able to supply the entire United States annual demand. Due to the well-developed dairy technology, one advantage of the present invention is that a low capital investment needed for manufacturing of the milk.

In some embodiments, the present invention contemplates using naturally bred transgenic founder females carrying transgene constructs that target gene expression to the mammary gland and inducing milk production in non-pregnant transgenic females. Many different biochemical evaluations may be performed for milk composition analysis including, but not limited to, enzyme linked immunosorbent assay, quantitative Western Blot analysis, affinity and/or anion exchange chromatography. Verification and identification of transgenic swine may be performed by polymerase chain reaction of ear notch tissue DNA, wherein the results are confirmed by Southern Blot analysis. Alternatively, copy number and stability of the transgene chromosomal insertions may be determined by comparison of F0 and F1 generations.

Several recombinant proteins have been expressed in high quantities in the milk of transgenic animals. In some instances, this productivity may contribute to compromised mammary physiology because of the extraordinary demand placed on the mammary secretory cells. For example, a transgenic goat expressing recombinant human butyrylcholinesterase in milk demonstrated the following disruptions in homeostatic mammary function: i) decreased milk production; and ii) reduced milk fat content. Although it is not necessary to understand the mechanism of an invention, it is believed that these disruptions may be associated with the lipid secretory mechanism at the mammary epithelium level and/or an elevated level of leukocytes. Baldassarre et al., "Lactation performance of transgenic goats expressing recombinant human butyrylcholinesterase in the milk" *Transgenic Res.* 17 (1):73-84 (2008).

While other human proteins have been secreted in biologically active form into various bodily fluids. Velander et al., "High-level expression of a heterologous protein in the milk of transgenic swine using the cDNA encoding human protein C" *Proc Natl Acad Sci USA*. 89:12003-12007 (1992). These reports also discuss various disadvantages and problems that have prevented commercialization including, but not limited to: i) expression in very low quantities due to aberrant splicing of RNA (Clark et al., "Expression of human anti-hemophilic factor IX in the milk of transgenic sheep" *Bio/Technology* 7:487-492 (1989)); ii) partial proteolytic processing, especially of unprocessed forms (Lee et al., "Proteolytic processing of human protein C in swine mammary gland" *J Biochem.* 118:81-87 (1995); and Yarus et al., "Secretion of unprocessed human surfactant protein B in the milk of transgenic mice" *Transgenic Res.* 6:51-57 (1997)); iii) inefficiently γ-carboxylated forms (Drohan et al., "Inefficient processing of human protein C in the mouse mammary gland" *Transgenic Res.* 3:355-364 (1994)); or iv) differential glycosylation (Denman et al., "Transgenic expression of a variant of human tissue-type plasminogen activator in goat milk: Purification and characterization of the recombinant enzyme" *Bio/Technology* 9:839-843 (1991); and Paleyanda et al., "Transgenic pigs produce functional human factor VIII in milk" *Nature Biotechnology;* 15:971-975 (1997)). Consequently, for these reasons, it should not be assumed that transgenic proteins are produced by the mammary gland in a physiologically active form. Such assessments require an empirical approach, wherein the expressed transgenic protein requires verification of characteristics including, but not limited to, sequence, post-translational modifications, and functional activity.

IV. Detection Methodologies

A. Detection of RNA mRNA expression may be measured by any suitable method, including but not limited to, those disclosed below.

In some embodiments, RNA is detection by Northern blot analysis. Northern blot analysis involves the separation of RNA and hybridization of a complementary labeled probe. In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes. In still further embodiments, RNA (or corresponding cDNA) is detected by hybridization to a oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLI-TAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

B. Detection of Protein

In other embodiments, gene expression may be detected by measuring the expression of a protein or polypeptide. Protein expression may be detected by any suitable method. In some embodiments, proteins are detected by immunohistochemistry. In other embodiments, proteins are detected by their binding to an antibody raised against the protein. The generation of antibodies is described below.

Antibody binding may be detected by many different techniques including, but not limited to, (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radio-isotope labels, for example), Western blots, precipitation reactions, agglutination assays (e.g., gel agglutination assays, hemagglutination assays, etc.), complement fixation assays, immunofluorescence assays, protein A assays, and immuno-electrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

C. Detection Kits

In other embodiments, the present invention provides kits for the detection and characterization of proteins and/or nucleic acids. In some embodiments, the kits contain antibodies specific for a protein expressed from a gene of interest, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

V. Pharmaceutical Compositions and Formulations

The present invention further provides pharmaceutical compositions and/or formulations comprising the drug compounds or proteins described above. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on size, sex, and/or species to be treated, with the course of administration lasting from several days to several months. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

EXPERIMENTAL

Materials: Domperidone—GlaxoSmithKline-1 mg/ml.
Estradiol Cypionate 17β—ProLab Pharmacy (Paris, Tex.)
Estradiol Cypionate LA—BET Pharmacy (Lexington, Ky.)—50 mg/ml
Matrix™—Intervet (Millsboro, Del.)—2.2 mg/ml.
Oxytocin—Baxter—10 units/ml.

Example I

17β-Estradiol/Oxytocin Induction

Two non-pregnant 450 lb nulliparous gilt swine (12 months old) were conditioned on an oral altrenogest paste formulation for 14 days (Matrix™, 2.2 mg/ml @ 7.5 ml/day, Intervet, Millsboro, Del.). After the 14 day conditioning period, a 3 cc intramuscular injection of 17β-estradiol (5 mg/ml; ProLab Laboratories) was given daily for seven (7) days. Twelve days after the last 17β-estradiol injection, a 5 cc intramuscular injection of oxytocin was administered. This protocol failed to induce any milk production in either animal.

Example II

Domperidone/Oxytocin Induction

A non-pregnant 450 lb first litter gilt swine (15 months old) was orally administered 5 mls of domperidone. Twenty-four hours later, a 5 cc intramuscular injection of oxytocin was administered. Twelve hours later, a 10 cc intramuscular injection of oxytocin was administered. This protocol failed to induce any milk production.

Example III

Domperidone/Oxytocin Induction

A non-pregnant 550 lb fifth parity sow (3.5 years old) was orally administered 5 mls of domperidone. Twenty-four hours later, a 5 cc intramuscular injection of oxytocin was administered. Twelve hours later, a 10 cc intramuscular injection of oxytocin was administered. This protocol failed to induce any milk production.

Example IV

17β-Estradiol Cypionate/Domperidone/Oxytocin Induction

A non-pregnant 240 lb gilt swine (five months old) was injected daily with a 3 ml composition containing 50 mg/ml of 17β-Estradiol Cypionate. Fourteen days later, an orally administered paste comprising 5 ml domperidone was administered. Twelve hours after the last domperidone administration, a 5 ml intramuscular injection of oxytocin was administered. This protocol failed to induce any milk production.

Example V

17β-Estradiol/Dexamethasone Induction

A non-pregnant fourteen month old gilt swine (ID: 7116) was administered an altrenogest composition (Matrix™, 2.2 mg/ml @ 7.5 ml/day, Intervet, Millsboro, Del.). and an intramuscular injection of 5 mg/kg of 17β-Estradiol Cypionate on a daily basis during Days 1-7. On Days 18-20, an intramuscular injection of 20 mg dexamethasone was administered. This protocol failed to induce any milk production.

Example VI

17β-Estradiol/Dexamethasone/Oxytocin Induction

A non-pregnant sow (ID: 6095) was administered an altrenogest composition (Matrix™, 2.2 mg/ml @ 7.5 ml/day, Intervet, Millsboro, Del.) and an intramuscular injection of 1 mg/kg of 17β-Estradiol Cypionate on a daily basis during Days 1-7. On Days 18-20, an intramuscular injection of 20 mg dexamethasone was administered. On Day 21 a 5 ml intramuscular injection of oxytocin was administered. This protocol resulted in the production of an insignificant amount of milk, but not enough for collection and analysis.

Example VII

17β-Estradiol/Dexamethasone/Oxytocin Induction

A non-pregnant sow (ID: Y3.4) was administered an altrenogest composition (Matrix™, 2.2 mg/ml @ 7.5 ml/day, Intervet, Millsboro, Del.) and an intramuscular injection of 5 mg/kg of 17β-Estradiol Cypionate on a daily basis during Days 1-7. On Days 18-20, an intramuscular injection of 20 mg dexamethasone was administered. On Day 21 a 5 ml intramuscular injection of oxytocin was administered. This protocol resulted in the production of 20 ml of milk on Day 21. However, no milk production was observed on Day 22 or after.

Example VIII

Estradiol (BET)/Domperidone/Oxytocin Induction

A non-pregnant sow (ID: DRU) was orally administered 3 ml of Estradiol Cypionate (BET) on Day 1. On Day 14 the sow as orally administered 5 ml of a gel comprising domperidone. On Day 15, the sow was administered a single intramuscular injection of oxytocin, after which an abundance of milk was produced.

Example IX

Litter Nursing by Induced Lactation

The lactating sow (ID: DRU) induced in accordance with Example VIII was administered 3 ml oxytocin on a daily basis, during which time a litter of six piglets were presented for nursing. The induced lactation continued unabated such that the sow successfully nursed six pigs for ten days. The piglets appeared healthy with weight gains comparable to normal parturition lactation nursing and no side effects were observed.

Example X

Estradiol (BET)/Domperidone/Oxytocin Induction of Lactation in a Sow

A non-pregnant transgenic prothrombin sow (ID: Granny) was orally administered 3 ml of Estradiol Cypionate (BET) on Day 1. On Day 14 the sow as orally administered 5 ml of a gel comprising domperidone. Starting on Day 15, the sow was administered a single intramuscular injection of oxytocin on each day of milk collection. Milk collection continued for an additional twenty days during which an abundance of milk was produced. See, FIG. 1.

Example XI

Estradiol (BET)/Domperidone/Oxytocin Induction of Lactation in a Gilt

A non-pregnant transgenic prothrombin gilt (ID: Sis) was orally administered 3 ml of Estradiol Cypionate (BET) on Day 1. On Day 14 the gilt as orally administered 5 ml of a gel comprising domperidone. Starting on Day 15, the gilt was administered a single intramuscular injection of oxytocin on each day of milk collection. Milk collection continued for an additional twenty-two days during which an abundance of milk was produced. See, FIG. 2.

Example XII

Swine Breeding

Transgenic swine females of breeding age may be bred three times using a non-transgenic boar during estrus. If conception is not obtained, and the female returns to estrous, super-ovulation may be induced by an oral administration of 7.5 ml/day of Matrix™ (Intervet, DE) for 22 days, followed by 7.5 ml injection of PG 600 on Day 23, and 72 hours later an injection of 1,000 IU of human chorionic gonadotropin (hCG). Upon showing estrus she will be bred to a non-transgenic boar On Day 54 post-conceptus the swine female may be treated with 7.5 ml/day of Matrix™, to aid in the maintenance of pregnancy. Pregnancy may be confirmed by ultrasound on approximately Day 30, 42 and 65 post-conceptus, wherein 7.5 ml/day of Matrix™ treatment will continue until pregnancy Day 109. The presence of skeletal formations will be used as a positive indicator of pregnancy.

Parturition may be induced if birth has not occurred by pregnancy Day 114. Parturition may be induced by administration of 15 mg of prostaglandin (Lutalyse®) and 12 mg of dexamethasone. Delivered piglets may be allowed to nurse on postpartum Day 1 through Day 3, and then can be cross-fostered to a surrogate sow.

Example XIII

Milk Collection

The pigs may be milked between approximately Days 1-50 after completion of the lactation induction protocol (i.e., for example, immediately after the oxytocin injection). A surrogate sow may be used for comparative purposes. If necessary, piglets may be separated from the sow for 30 minutes. Udder washing may also be conducted using a mixture of 1 ml of BioWay Blue Udder Wash® with 16 oz of water. After clearing out the teats, milk can be collected. Optionally, the collection device may contain 6-aminocaproic acid (ACA), aprotinin and/or benzamidine.

The collected milk may be pooled, wherein 200 mM EDTA is added at a 1:1 ratio with the milk. Subsequently, the collected milk is put into date-labeled sterile containers, frozen at −40° C. until analysis.

Example IVX

General Milk Composition Analysis

Milk samples are collected in accordance with Example XII. These samples are then assayed for lactose, protein, and fat using standard automated procedures. For example, a Mutidpec Infared Dairy Product Analyzer is compatible with the needs and requirements to complete these assay procedures. Samples may also be assayed by an electronic somatic cell counter (i.e., for example, a Fossomatic 5000). Concentrations of α-lactalbumin may be measured by radioimmunoassay. Akers et al., "Radioimmunoassay for measurement of bovine alpha-lactalbumin in serum, milk and tissue culture media" *J Dairy Res.* 53 (3):419-429 (1986). Milk yield data may be obtained from according to previously described methods. Clowes et al., "Feeding lactating primiparous sows to establish three divergent metabolic states: II. Effects on nitrogen partitioning and skeletal muscle composition" *J Am Sci.* 76:1154-1164 (1998).

Example XV

Milk Composition from Chemically Induced Lactation

The milk collected in accordance with either Example X (Granny) or Example XI (Sis) was diluted with water in an approximate 1:1 ratio, wherein a preliminary evaluation of composition was performed. The chemically induced milk samples were compared to non-induced control milk sample (lactation day 36) and an induced control milk (lactation day 1)

Color:
  Granny: Slight yellow tint unlike the cream-colored non-induced control milk.
  Sis: More yellow than either Grandma's or the control milk.
Viscosity:
  Granny: Slightly less viscous than the non-induced control milk.
  Sis: Similar to water.
  Induced Control milk: Intermediate between Sis and Granny's.
Turbidity:
  Granny: Similar to non-induced control milk.
  Sis: Yellow-colored particulates.
  Induced control milk: Particulates.
Fat Content:
  Grandma and Sis' milks and the induced control milk had similar levels of fat content but significantly less than that contained in the non-induced control milk.

Example XV

Milk Volumes from Chemically Induced Lactation

Factor 8 (1), & Factor 9 (2) Landrace gilts (foster mothers; approx. 1.5 years of age) were treated with the induction protocol described above. These gilts had undergone eight conception attempts but were unable to concieve. The lactation induction protocol described above, successfully induced lactation in each gilt to support 4 pigs on each gilt for 30 days. The Factor 8 gilt under went collection of between 5-10 ml of mild for fifteen days. The first Factor 9 gilt underwent collection of between 1-2 mls per day for the first several days. The second Factor 9 gilt underwent collection of between 10-20 mls milk per day for thirty days.

I claim:
1. A method, comprising:
  a) providing;
    i) a first composition comprising an estrogen compound, wherein said first composition is a pharmaceutically acceptable formulation;
    ii) a second composition comprising a dopaminergic antagonist, wherein said second composition is a pharmaceutically acceptable formulation;
    iii) a third composition comprising oxytocin, wherein said third composition is a pharmaceutically acceptable formulation;
    vi) a non-pregnant transgenic non-human mammal; and
  b) sequentially administering to said transgenic mammal;
    i) a single dose of said first composition to said mammal;
    ii) a single dose of said second composition to said mammal on a different day after said single dose of said first composition; and
    iii) a single dose of said third composition to said mammal on at least one day after said second composition.
2. The method of claim 1, further comprising step (e) collecting a commercially viable volume of milk from said mammal.
3. The method of claim 1, wherein said second composition is administered fourteen days after said first composition.
4. The method of claim 1, wherein said third composition is administered twenty-four hours after said second composition.
5. The method of claim 1, wherein said first composition is administered orally.
6. The method of claim 1, wherein said second composition is administered orally.
7. The method of claim 1, wherein said third composition is administered parenterally.
8. The method of claim 7, wherein said parenteral administration comprises an intramuscular injection.
9. The method of claim 6, wherein said oral administration comprises a gel.
10. The method of claim 2, wherein said milk is collected on the same day as said oxytocin administration.
11. The method of claim 1, wherein said non-pregnant mammal is a female.
12. The method of claim 1, wherein said non-pregnant mammal is a male.
13. The method of claim 11, wherein said female mammal is nulliparous.
14. The method of claim 11, wherein said female mammal has not been pregnant for at least six months.
15. The method of claim 11, wherein said female mammal has not been pregnant for at least twelve months.
16. The method of claim 11, wherein said female mammal has delivered at least one litter.
17. The method of claim 11, wherein said female mammal is a virgin.
18. The method of claim 11, wherein said female mammal is prepubertal.
19. The method of claim 1, wherein said estrogen compound is long acting.

* * * * *